(12) United States Patent
Iskra

(10) Patent No.: US 6,465,256 B1
(45) Date of Patent: Oct. 15, 2002

(54) DEVICE AND METHOD FOR SEPARATING COMPONENTS OF A FLUID SAMPLE

(75) Inventor: Michael J. Iskra, Bridgewater, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 66 days.

(21) Appl. No.: 09/649,402

(22) Filed: Aug. 26, 2000

(51) Int. Cl.[7] .................................................. G01N 1/18
(52) U.S. Cl. ...................... 436/177; 210/789; 422/72; 422/101; 422/102; 436/45; 436/63
(58) Field of Search ................................. 422/101, 102, 422/72; 436/177, 63, 45; 210/512.1, 512.3, 787, 789

(56) References Cited

U.S. PATENT DOCUMENTS

| | | |
|---|---|---|
| 3,832,141 A | 8/1974 | Haldopoulos |
| 3,849,072 A | 11/1974 | Ayres |
| 3,919,085 A | 11/1975 | Ayres |
| 4,055,501 A | 10/1977 | Cornell |
| 4,083,788 A | 4/1978 | Ferrara |
| 4,088,582 A | 5/1978 | Murty et al. |
| 4,131,549 A | 12/1978 | Ferrara |
| 4,152,270 A | 5/1979 | Cornell |
| 4,154,690 A | 5/1979 | Ballies |
| 4,257,886 A | 3/1981 | Kessler |
| 4,294,707 A | 10/1981 | Ikeda et al. |
| 4,295,974 A | 10/1981 | Cornell |
| 4,308,232 A | 12/1981 | Crouther et al. |
| 4,315,892 A | 2/1982 | Stone et al. |
| 4,364,832 A | 12/1982 | Ballies |
| 4,417,981 A | 11/1983 | Nugent |
| 4,443,345 A | 4/1984 | Wells |
| 4,569,764 A | 2/1986 | Satchell |
| 4,770,779 A | 9/1988 | Ichikawa et al. |
| 4,818,386 A | 4/1989 | Burns |
| 4,853,137 A | 8/1989 | Ersson |
| 4,867,887 A | 9/1989 | Smith |
| 4,877,520 A | 10/1989 | Burns |
| 4,917,801 A | 4/1990 | Luderer et al. |
| 5,269,927 A | 12/1993 | Fiehler |
| 5,393,674 A | * 2/1995 | Levine et al. |
| 5,454,958 A | 10/1995 | Fiehler |
| 5,455,009 A | 10/1995 | Vogler et al. |
| 5,575,778 A | 11/1996 | Hardt et al. |
| 5,632,905 A | 5/1997 | Haynes |
| 5,707,876 A | 1/1998 | Levine |
| 5,736,033 A | 4/1998 | Coleman et al. |
| 5,860,937 A | 1/1999 | Cohen |
| 6,063,297 A | 5/2000 | Antanavich et al. |

FOREIGN PATENT DOCUMENTS

| | | |
|---|---|---|
| EP | 0 017 127 | 10/1980 |
| EP | 0 627 261 A2 | 12/1994 |
| EP | 0 638 804 A1 | 2/1995 |
| EP | 0 875 202 A2 | 11/1998 |
| EP | 1 107 002 A2 | 6/2001 |
| JP | 56-168847 | 12/1981 |
| JP | 6-222055 | 8/1994 |

* cited by examiner

Primary Examiner—Jan Ludlow
(74) Attorney, Agent, or Firm—Nanette S. Thomas

(57) ABSTRACT

A device and method for separating heavier and lighter phases of a fluid sample is described. The fluid separation device includes an elongate collection tube accommodating the fluids, and a deformable separator including a deformable bladder having a flowable substance contained therein. The deformable bladder is reconfigurable upon centrifugation to a toroidal shape allowing fluid flow therethrough. The bladder is movable along the tube during centrifugation to a position between the separated blood phase.

15 Claims, 3 Drawing Sheets

DEVICE AND METHOD FOR SEPARATING COMPONENTS OF A FLUID SAMPLE

BACKGROUND OF THE INVENTION

1. Field of the Invention

This invention relates to a device and method for separating heavier and lighter fractions of a fluid sample. More particularly, this invention relates to a device and method for collecting and transporting fluid samples whereby the device and fluid sample are subjected to centrifugation in order to cause separation of a heavier fraction from a lighter fraction of a fluid sample.

2. Description of Related Art

Diagnostic tests may require separation of a patient's whole blood sample into components, such as serum or plasma, a lighter phase component, and red blood cells, a heavier phase component. Samples of whole blood are typically collected by venipuncture through a cannula or needle attached to a syringe or an evacuated collection tube. Separation of the blood into serum or plasma is then accomplished by rotation of the syringe or tube in a centrifuge. Such arrangements use a barrier for moving into an area adjacent the two phases of the sample being separated to maintain the components separated for subsequent examination of the individual components.

A variety of devices have been used in collection containers to divide the area between the heavier and lighter phases of a fluid sample. Many of these devices include mechanical barriers or partitions which are positioned within the lower collection tube. Upon centrifugation, the barrier becomes relocated within the tube between the separated blood phases.

Other separators include the use of thixotropic gel materials such as polyester gels in a tube. Such polyester gel serum tubes require special manufacturing equipment to prepare the gel and to fill the tubes. Moreover, the shelf-life of the product is limited in that, over time, globules may be released from the gel mass. These globules have a specific gravity that is less than the separated serum and may float in the serum and may clog certain measuring instruments, such as the instrument probes used during the clinical examination of the sample collected in the tube. Such clogging can lead to considerable downtime for the instrument to remove the clog.

No commercially available gel is completely chemically inert to all analytes. If certain drugs are present in the blood sample when it is taken, there can be an adverse chemical reaction with the gel interface.

Therefore, a need exists for a separator device that (i) is easily and inexpensively manufactured; (ii) is easily used to separate a blood sample; (iii) is independent of temperature during storage and shipping; (iv) is stable to radiation sterilization; (v) employs the benefits of a thixotropic gel barrier yet avoids the many disadvantages of placing a gel in contact with the separated blood components; (vi) minimizes cross contamination of the heavier and lighter phases of the sample during centrifugation; (vii) minimizes adhesion of the lower and higher density materials against separator device; (viii) is able to move into position to form a barrier in less time than conventional methods and devices; (ix) is able to provide a clearer specimen with less cell contamination than conventional methods and devices; and (x) can be used with standard sampling equipment.

SUMMARY OF THE INVENTION

The present invention provides a fluid separation device for maintaining separation of centrifuged fluids having first and second phases of respective densities. The device includes an elongate collection tube for accommodating fluids, and a deformable separator disposed within said tube. The separator is a ring-shaped bladder, having a configuration including a tubular passage for movement of the fluids therethrough. The bladder contains a flowable substance with a density intermediate the densities of the first and second phases of the fluids. The bladder furthermore is movable upon centrifugation to a position between separated first and second phases of the fluids, and is reconfigurable after centrifuge into a disk-like configuration along the tubular passage, establishing a separation between the first and second phases of the fluids.

The present invention also provides a method of separating and maintaining separation of fluids of first and second phases of respective densities. The method of separating collected blood fluids in heavy and light phases comprises the steps of first providing an elongate blood collection tube having a deformable separator resident therein. The deformable separator is generally toroidal in shape and contains a medium therein with a density such that the density of the bladder and medium combined is intermediate the respective densities of said heavy and light fluid phases. Collected blood fluids are placed in the tube and the tube is centrifuged to cause blood separation into said heavy and light phases. Centrifugation also causes the deformable separator to move in-between the phases and reconfigure from the generally toroidal shape having a passage therethrough for passage of fluids to a disk-like shape, which maintains separation between said separated phases of said fluids.

The device of the present invention is advantageous over existing separation devices in that it provides a more efficient separation of different phases of blood by the deformable bladder walking up the sides of the cylinder collection tube, while allowing flow of heavier fluids and cellular material through a central tubular passage of the separator.

A particular advantage of the device is that there is no shearing of the clot, as it is moving in the same direction as the inside of the toroidal-shaped tubular separator. The speed of the movement may be dictated by how quickly the clot separates and forms a density gradient, but can also be modified by the type of gel, or other substance used within bladder. For example, the lower the viscosity, the faster the movement of the separator, and hence the quicker the separation.

Furthermore, the deformable separator is advantageous to use, in that it has great tolerance variations due to its deformability. For example, it may be used with many different elongate collection tubes as it is highly tolerant to any variations between different tubes. Since it is essentially a deformable bladder, the separator adjusts easily to the collection tube, and is malleably positioned in both disk-like and toroidal configuration.

DETAILED DESCRIPTION

The present invention may be embodied in other specific forms and is not limited to any specific embodiments described in detail, which are merely exemplary. Various other modifications will be apparent to and readily made by those skilled in the art without departing from the scope and spirit of the invention. The scope of the invention will be measured by the appended claims and their equivalents.

The present invention is a fluid separation device for maintaining separation of centrifuged fluids having first and second densities. Preferably the fluids are blood fluids. Blood is typically collected and separated into the lighter phase (serum or plasma) and the heavier phase (red blood cells and other cellular material) for testing and diagnoses.

Figure 1:
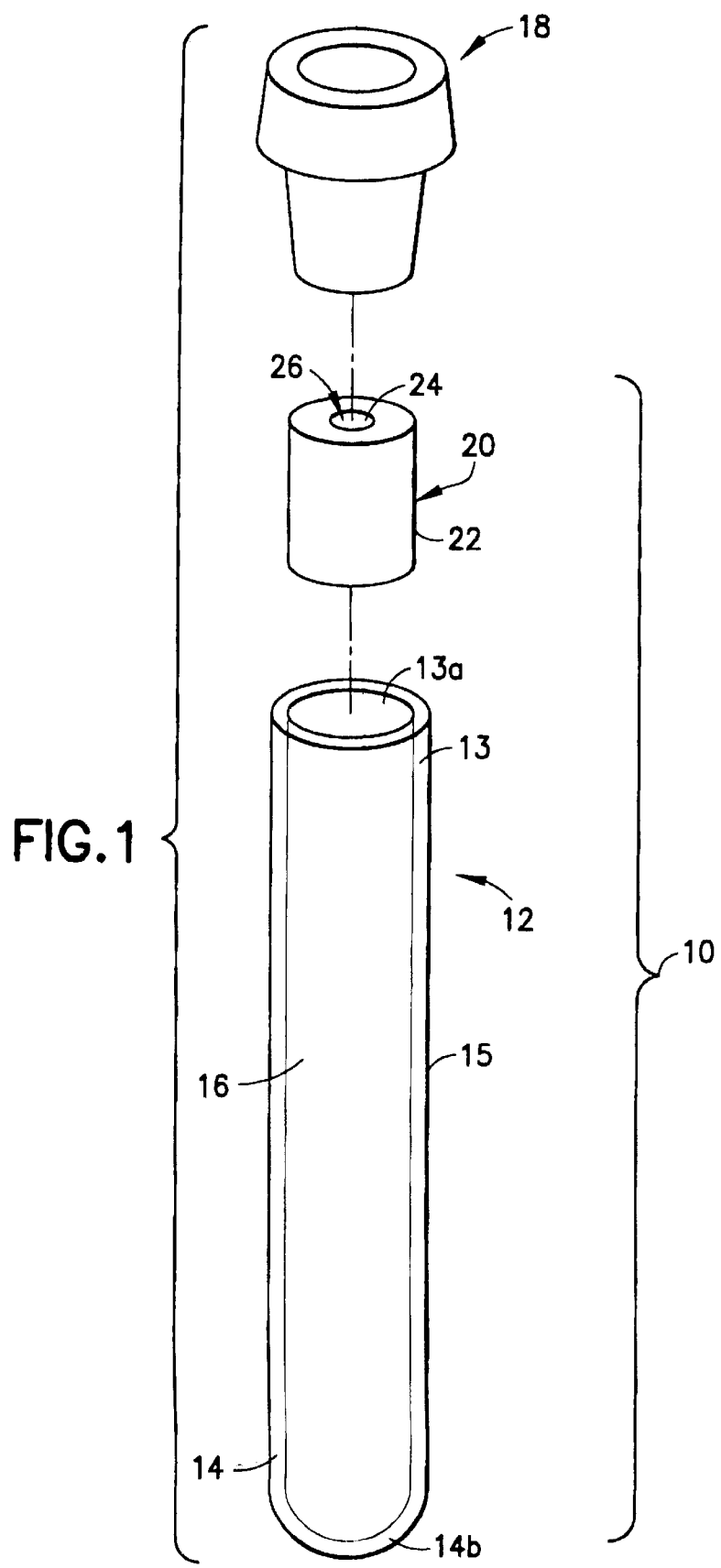
FIG. 1 is a perspective view of the fluid separation device of the present invention including a blood collection tube and deformable separator.
Figure 2:
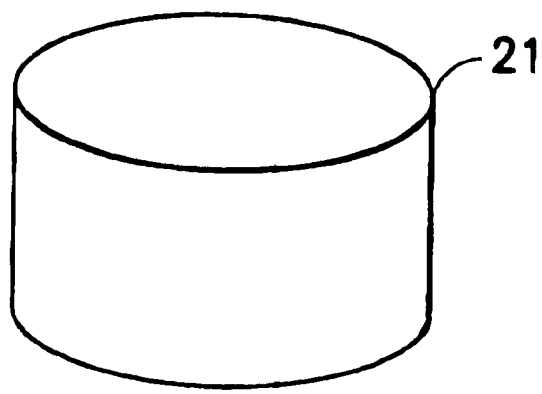
FIG. 2 is a perspective view of the separator in its resting configuration when no force is acted upon it.

Referring now to FIGS. 1 and 2 of the drawings, a fluid separation device 10 of the present invention is shown. Fluid separation device 10 includes an elongate collection tube 12 of generally conventional construction. Tube 12 is an elongate cylindrical member having an upper end 13, a lower end 14, and a cylindrical wall 15 extending therebetween. The upper end 13 includes an opening 13a, while the lower end 14 is closed by an integrally formed bottom 14a. A tube interior 16 is defined between upper and lower ends 13 and 14. The opening 13a of upper end 13 of tube 12 may be closed by a conventional stopper 18 which is made of a suitable elastomer such as rubber. Stopper 18 may be pierceable by a needle cannula (not shown) for permitting introduction of collected blood into the interior of tube 12.

Disposed within tube 12 is a deformable separator 20. Deformable separator 20 is defined by a ring-shaped bladder 21. The bladder 21 forming deformable separator 20 is generally in the configuration of a toroidal-shaped tube having an outer tubular wall 22 connected continuously to an inner tubular wall 24. Inner tubular wall 24 defines an openable tubular passage 26 through bladder 21. As will be described herein below, bladder 21 is reconfigurable to two operative shapes in the present invention. One shape maintains tubular passage 26 open so as to permit fluid flow therethrough and the other shape is in the form of a solid disk closing tubular passage 26 and preventing fluid flow therethrough.

Separator 20 includes a flowable substance 28 within bladder 21. Flowable substance 28 has a density intermediate the densities of the first and second phases of the fluids being centrifuged for separation. Flowable substance 28 is preferably a thixotropic substance which is rendered flowable upon centrifuge of the fluid separation device.

Bladder 21 may be formed of a material having a high coefficient of friction. Such material would have a tendency to adhere to the inner wall of the collection tube. Due to this frictional adhesion and the toroidal shape taken by the bladder upon centrifugation, the bladder has a tendency to "walk" along the wall of the tube by rolling over itself rather than by sliding therealong. This provides a separation of fluids in a more proficient manner. This high coefficient of friction may be provided by selecting an appropriate material forming the bladder 21. Also, a coating may be applied to the bladder to provide adhesion to the walls of the tube. Such a coating is inert to the blood to be separated.

Bladder 21 may be a flexible deformable bladder which is reconfigurable upon an application of force (e.g., centrifuge, as mentioned above). Bladder 21 may be formed from a wide variety of both elastic and inelastic materials such as polyethylene, polyurethane, or syran. The particular material which forms bladder 21 is selected so that the material does not adversely interact with the fluids (e.g., blood) which would come in contact with the bladder. The diameter of the bladder is selected such that it fits snugly within collection tube 12. Bladder 21 is formed of a material which is sufficiently deformable, flexible, and pliable, but also has sufficient strength so as to permit bladder deformation without risk of rupturing of the bladder. Bladder 21 may be formed from polyethylene, polyurethane, syran or latex.

Flowable substance 28 is contained within bladder 21 in sealed containment. Substance 28 may preferably be a gel introduced into bladder 21 upon evacuation of bladder 21. Flowable substance 28 is a thixotropic medium which may be subject to fluid flow upon introduction of a force thereto. Generally, contact between substance 28 and the blood is prevented by bladder 21, but it is still preferred that substance 28 be substantially water insoluble and be inert to components of the blood.

Substance 28 is selected so that it becomes resident between the separated blood phases. Thus, substance 28 is selected to have a specific gravity when combined with the bladder, intermediate the specific gravities of the separated lighter serum or plasma phase, and the heavy cellular phase. When separating phases in blood, it is preferable to use a substance 28 with a density of between 1.030 g/cc and 1.06 g/cc, and it is most preferable to use a substance with a density of 1.045 g/cc, which is intermediate the densities of red blood cells and serum. Substance 28 is generally fluid in nature. However, at rest and under normal handling and shipping conditions, it may be semi-solid or resistant to flow. When subjected to forces such as centrifugal forces, substance 28 becomes flowable. Upon cessation of such centrifugal forces however, substance 28 may return to its more solid or non-flowable state.

Substance 28 may be selected from the group consisting of gels, oils, silicones, and combinations thereof. Substance 28 may be a single component gel or may be formed of various combinations of gels and fluids. Examples include mixtures of silicon and hydrophobic silicon dioxide powders, or mixtures of liquid polybutane polymer and silicon dioxide powder. The gels may also contain a flow-promoting substance mixed therein. The gel may also contain particulate matter mixed in combination therewith, particularly beads.

Figure 3:
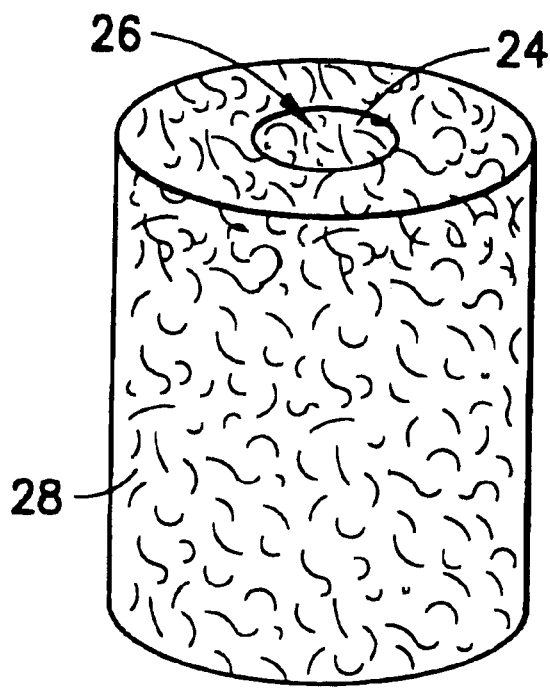
FIG. 3 is a perspective view of the separator shown in FIG. 2 with a centrifugal force applied thereto.

With reference to FIGS. 2 and 3 of the drawings, ring-shaped bladder 21 is shown at rest in FIG. 2, and is shaped as a flat annular disk-shape with tubular passage 26 closed, or obstructed. In this configuration, it may serve as a barrier through which fluids may not flow. Upon application of a centrifugal force however, bladder 21 reconfigures into a toroidal-shaped tube as shown in FIG. 3, with tubular passage 26 defined by inner tubular wall 24.

Figure 4:
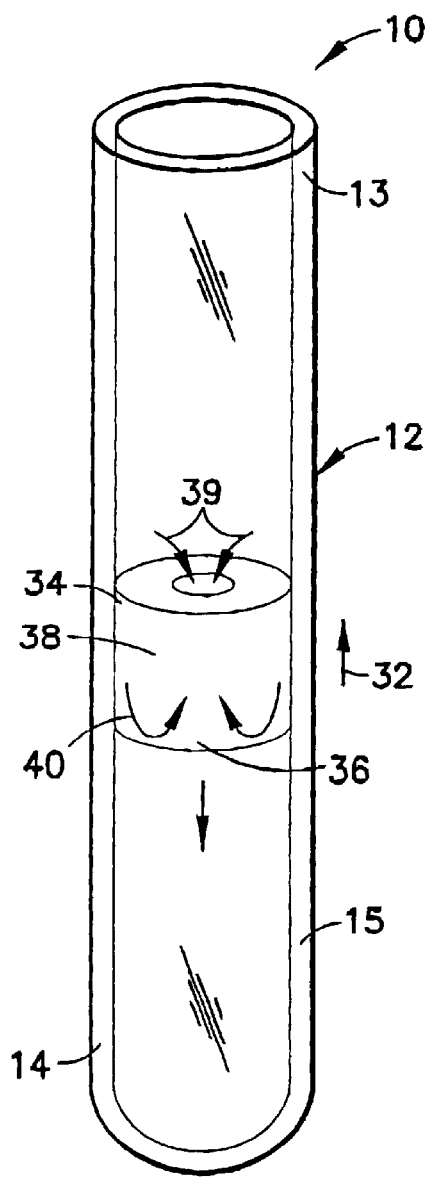
FIG. 4 is a perspective view of the device of the present invention as centrifugal force is applied thereto.
Figure 5:
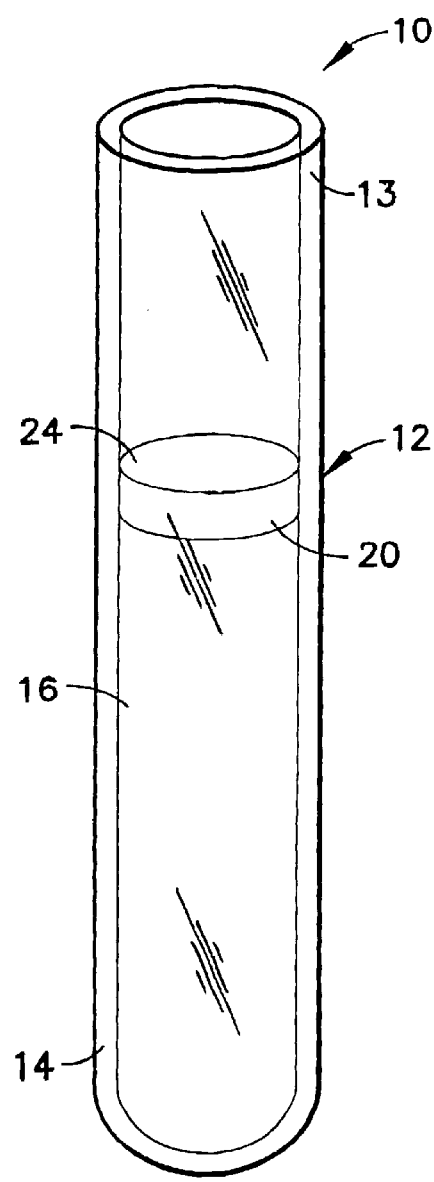
FIG. 5 is a perspective view of the separation device of the present invention at rest after centrifuge.

Prior to use of the fluid separation device 10, the deformable separator 20 is inserted into tube 12. The gel containing bladder is positioned in the lower end 14 of tube 12. After withdrawal of blood, the blood is then injected into tube 10. With reference now to FIGS. 4 and 5 of the drawings, the tube is then subjected to centrifuge. Upon centrifuge, bladder 21 reconfigures to a toroidal shaped tube with outer tubular wall 22 continuously connected to inner tubular wall 24, defining a tubular passage 26 therethrough. The toroidal tube contains an upper end 34 and a lower end 36 and a center of gravity 38 in the middle therebetween. Separator 20 moves up through collection tube 12 from lower end 14 towards upper end 13 in a direction indicated by directional arrow 32. As separator 20 moves upward within tube 12, the more dense red blood cells flow through tubular passage 26 in a direction as indicated by directional arrows 39. As noted above, bladder 21 preferably moves within tube 12 by a frictionless, rolling mechanism. In rolling the toroidal tube up the cylindrical walls of tube 12, the outer tubular wall 22 rolls to the lower end 36 of separator 20 to replace inner tubular wall 24 similar to a mobius strip. The direction of the rolling movement of the wall is indicated by directional arrows 40. Preferably the movement is accompanied by the absence of sliding between outer wall 22 and cylindrical walls 15 of collection tube 12. This provides a more efficient migration of separator 20, and, subsequently, a more efficient separation of fluids.

This rolling mechanism coupled with a slight adhesion of outer wall 22 to the cylindrical walls of tube 12 provide an efficient "walking" migration of the separator up the tube, with the more dense red blood cells flowing through the tube's center to the bottom of the tube. Bladder 21 substantially clings to the sides of the tube, which provides tubular passage 26 as the only alternative downward direction where the clot is able to flow. The central aperature in the bladder provides a funnel like entrance for the higher density clot and cellular material to flow.

Upon cessation of the centrifuge process, bladder 21 then reverts to its disk-like configuration with tubular passage 26 being obstructed as seen in FIG. 5. Separator 20 is now at rest between the red blood cells of lower density, and the serum of higher density, and provides a barrier therebetween by obstruction of tubular passage 26.

What is claimed is:

1. A fluid separation device for maintaining separation of centrifuged fluids having first and second phases of respective densities, said device comprising:
   an elongated collection tube for accommodating said fluids; and
   a deformable separator disposed within said tube, said separator comprising a bladder containing a deformable and flowable substance with a density intermediate the densities of the first and second phases of said fluids, said bladder having a configuration during centrifugation being generally ring shaped having a tubular passage for movement of fluids therethrough, said bladder being movable during said centrifugation to a position between said separated first and second phases of said fluids and being reconfigurable after said centrifuge into a disk-like configuration along said tubular passage and establishing a separation between said first and second phases.

2. The device of claim 1, wherein said deformable separator is a toroidal shaped tube with an outer tubular wall connected continuously to an inner tubular wall defining said tubular passage through said inner tubular wall, said toroidal tube containing an upper end and a lower end, and a center of gravity therebetween, and wherein said separation of said fluid phases is established with said tubular passage within said separator being obstructed.

3. The device of claim 2, wherein said separator moves along cylindrical walls of said elongate collection tube in a rolling mechanism, wherein said outer tubular wall of said separator rolls to the lower end of said toroidal tube as said center of gravity of said separator rises upon centrifuge.

4. The device of claim 3, wherein said bladder of said separator is formed of a material selected from the group consisting of polyethylene, polyurethane, syran and latex.

5. The device of claim 1, wherein said flowable substance within said separator is a thixotropic substance rendered flowable upon centrifugal forces.

6. The device of claim 5, wherein said thixotropic fluid includes a flow promoter.

7. The device of claim 5, wherein said flowable substance is selected from the group consisting of gels, oils, silicones, and combinations thereof.

8. The device of claim 1, wherein said fluids are blood fluids.

9. The device of claim 8, wherein said flowable substance has a density between 1.030 g/cc and 1.060 g/cc.

10. The device of claim 9, wherein said flowable substance has a density of 1.045 g/cc.

11. A method of separating collected blood fluids in heavy and light phases comprising the steps of:
   providing an elongate blood collection tube having a deformable separator resident therein, said deformable separator being generally toroidal in shape and containing a medium therein with a density intermediate the respective densities of said heavy and light phase fluids;
   placing said collected blood fluids in said tube; and
   centrifuging said tube to cause blood separation into said heavy and light phases and causing said deformable separator to move in between said phases by reconfiguring said separator between said toroidal shaping having a passage therethrough for passage of said fluids, and a disk-like shape to maintain separation between said separated phases of said fluids.

12. The method of claim 11, wherein said deformable separator is a toroidal tube with an outer tubular wall connected continuously to an inner tubular wall defining a tubular passage through said inner tubular wall, said toroidal tube containing an upper end and a lower end, and a center of gravity therebetween, and wherein said separation of said fluid passages is established with said tubular passage within said separator being obstructed.

13. The method of claim 12, wherein said centrifuging step causes said separator to move along cylindrical walls of said elongate collection tube in a rolling mechanism, wherein said outer tubular wall of said separator rolls to the lower end of said toroidal tube as said center of gravity of said separator rises upon centrifuge.

14. The method of claim 11, wherein said medium is a thixotropic substance rendered flowable upon said centrifugation.

15. The method of claim 12, wherein said toroidal tube is formed of a material selected from the group consisting of polyethylene, polyurethane, syran and latex.

* * * * *